United States Patent [19]

Schaefer et al.

[11] Patent Number: 5,043,152
[45] Date of Patent: Aug. 27, 1991

[54] IODINATED NON-IONIC TRIIODOBENZENE COMPOUNDS AND CONTRAST MEDIA CONTAINING THEM

[75] Inventors: Michel Schaefer, Chilly-Mazarin; Maryse Dugast-Zrihen; Michel Guillemot, both of Paris; Didier Doucet, Livry-Gargan; Dominique Meyer, Paris, all of France

[73] Assignee: Guerbet S.A., Villepinte, France

[21] Appl. No.: 480,980

[22] Filed: Feb. 16, 1990

Related U.S. Application Data

[63] Continuation-in-part of Ser. No. 360,203, Jun. 1, 1989, abandoned.

[30] Foreign Application Priority Data

Jun. 2, 1988 [FR] France .................. 88 07369
Jan. 23, 1989 [FR] France .................. 89 00762
Jan. 5, 1990 [FR] France .................. 90 00106

[51] Int. Cl.$^5$ .................................. A61K 49/04
[52] U.S. Cl. ........................ 424/5; 564/153; 564/156
[58] Field of Search ............ 564/153, 156; 424/5

[56] References Cited

U.S. PATENT DOCUMENTS 3,701,771 10/1972 Almen et al. .................. 564/153
4,364,921 12/1982 Speck et al. .................. 564/153
4,396,598 8/1983 Lin .................................. 424/5
4,474,747 10/1984 Dimo et al. .................... 424/5

FOREIGN PATENT DOCUMENTS 0345163 6/1989 European Pat. Off. .
3429949 2/1986 Fed. Rep. of Germany ...... 564/153

Primary Examiner—Richard L. Raymond
Assistant Examiner—Scott C. Rand
Attorney, Agent, or Firm—Young & Thompson

[57] ABSTRACT

The invention relates to novel non-ionic compounds of formula

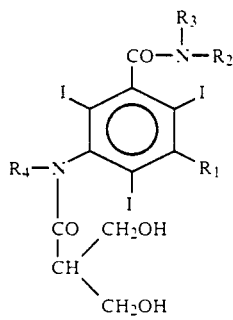

These compounds can be used as contrast media.

12 Claims, No Drawings

IODINATED NON-IONIC TRIIODOBENZENE COMPOUNDS AND CONTRAST MEDIA CONTAINING THEM

The present application is a continuation-in-part of U.S. Ser. No. 360,203 filed Jun. 1, 1989, now abandoned.

The present invention relates to compounds which can be used in contrast media for radiography.

Iodobenzene compounds containing several iodine atoms in the benzene nucleus, usually 3 iodine atoms per benzene nucleus, and various other substituents have been used for a long time as contrast medium. These other substituents are pharmacologically acceptable groups which enable the compounds to be administered to man and animals. Generally speaking, these substituents are chosen, on the one hand, in order to confer adequate solubility in water on the compound so that they can be administered in aqueous solution and, on the other, in order to confer on these compounds sufficient tolerance for them to be tolerated by the human organism.

For this purpose, non-ionic structures have been suggested, i.e. iodobenzene derivatives possessing non-ionic substituents.

Thus, in the patent FR-A-2 053 037, carbamoyl iodobenzene compounds containing a total of at least one N-hydroxy alkyl group and at least two hydroxy groups were suggested.

A compound illustrative of this class is metrizamide which has, however, proved to be of limited stability.

The present invention aims to provide novel non-ionic compounds which are well tolerated by the human organism, very stable in aqueous solution, which possess a high solubility in water and which exhibit low viscosity in solution.

To this end, the subject of the present invention is compounds of formula:

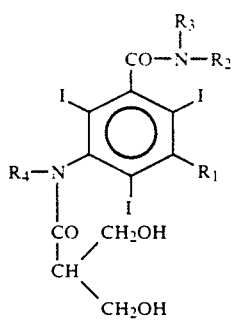

I in which $R_1$ is selected from a group of formula

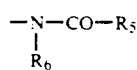

in which
  $R_5$ is selected from $C_1$-$C_4$ alkyl, $C_1$-$C_4$ hydroxyalkyl or $C_1$-$C_4$ polyhydroxyalkyl, and
  $R_6$ is selected from hydrogen, $C_1$-$C_4$ alkyl, $C_1$-$C_4$ hydroxyalkyl or $C_1$-$C_4$ polyhydroxyalkyl,
and a group of formula

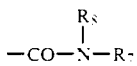

in which
  $R_7$ is selected from $C_1$-$C_4$ hydroxyalkyl or $C_1$-$C_4$ polyhydroxyalkyl, and
  $R_8$ is selected from hydrogen or $C_1$-$C_4$ alkyl,
  $R_2$ is selected from hydrogen, $C_1$-$C_4$ hydroxyalkyl or $C_1$-$C_4$ polyhydroxyalkyl,
  $R_3$ is selected from hydrogen or $C_1$-$C_4$ alkyl, and
  $R_4$ is selected from hydrogen, $C_1$-$C_4$ alkyl, $C_1$-$C_4$ hydroxyalkyl or $C_1$-$C_4$ polyhydroxyalkyl.

In the present invention by polyhydroxyalkyl group is meant a linear or branched polyhydroxyalkyl group.

A preferred compound of formula I is the compound of formula I in which

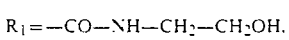

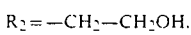

Moreover, a preferred group of compounds of formula I is that constituted by the compounds of the symmetrical diamino type, i.e. the compounds of formula:

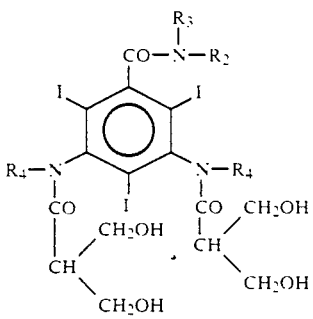

II the compounds of formula I can be prepared in a standard manner in particular by acylation and/or alkylation reactions starting from known compounds.

Thus, the compounds of the symmetrical diamino type (compounds of formula II) can be prepared by
  a) acylation of a diamino compound of formula:

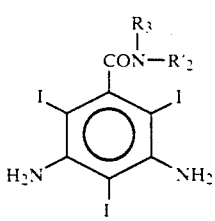

III $R_2'$ representing a $R_2$ group, the hydroxy groups of which have been protected, with an acid chloride of formula:

IV in which R represents

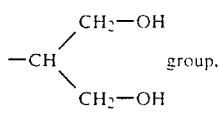 group, the hydroxy groups of which are protected,
b) alkylation of the compound obtained, if necessary, with an alkylating reagent of formula:

$$R'_4 Z \qquad \qquad V$$

in which $R'_4$ has the meanings given previously except hydrogen and Z represents a labile group such as an atom of chlorine, bromine or iodine, in the presence of a base such as sodium methylate, sodium ethylate, sodium hydride or sodium hydroxide.

c) deprotection

Compounds of formula III are described in the French patent application FR-A-2 614 299.

The other compounds of formula III can be prepared in an analogous manner starting in particular from an alkyl 3,5-dinitrobenzoate of formula:

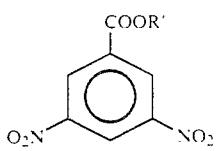

in which R' is a $C_1$–$C_4$ alkyl group such as methyl.

Asymmetric diamino compounds can also be prepared starting from a compound of formula VI by:

a) reaction with an amine of formula:

 VII so as to produce a compound of formula:

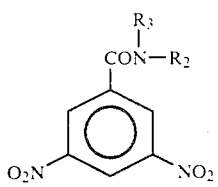

b) reduction by means of ammonium sulfide so as to give rise to a compound of formula:

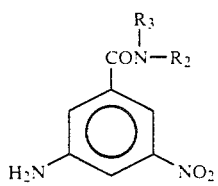

c) acylation of the compound of formula IX by an acid chloride of formula RCOCl (IV) so as to give rise to a compound of formula:

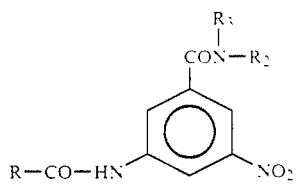

d) reduction and iodination of the compound of formula X so as to give rise to a compound of formula:

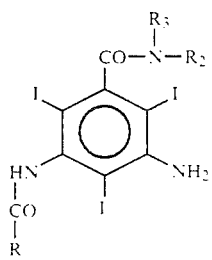

e) alkylation, if required, of the compound of formula XI with an alkylating reagent of formula V so as to give rise to a compound of formula:

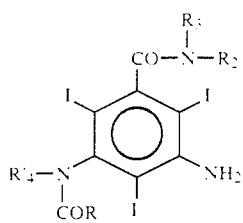

f) deprotection of the compound of formula XII g) acylation of the deprotected compound obtained with an acid chloride of formula:

$$Cl-CO-R'_5 \qquad \qquad XIII$$

$R'_5$ representing a group $R_5$, the hydroxy groups of which are protected, so as to give rise after deprotection to a compound of formula:

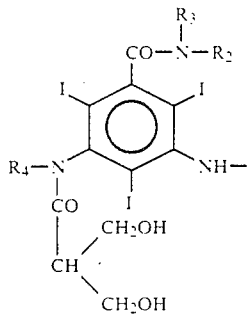

the steps f and g may be carried out in the reverse order, and if necessary h) alkylation to give rise to a compound of formula I in which $R_6$ has the meanings indicated except hydrogen.

Symmetrical compounds of the isophthalic type (compounds of formula I in which $R_1 = -CO-N-R_2)$
         |
         $R_3$ can be prepared by a) acylation of an amine of formula:

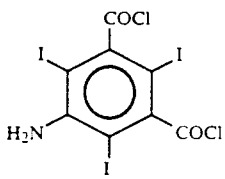 XV with an acid chloride of formula RCOCl (IV) so as to give rise to a compound of formula:

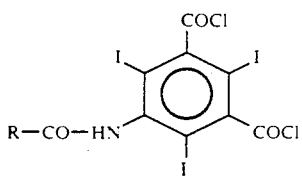 XVI b) reaction of the compound of formula XVI with an amine of formula

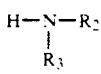 (VII)

so as to give rise to a compound of formula:

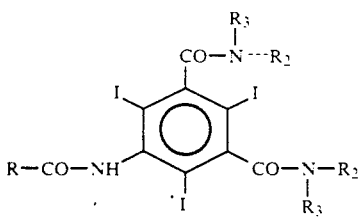 XVII then, if desired, either c) alkylation of the compound of formula XVII with an alkylating reagent of formula $R'_4Z$ such as that specified previously and finally d) removal of the protecting groups from the —CH(CH$_2$OH)$_2$ group, or e) removal of the protecting groups from the —CH(CH$_2$OH)$_2$ group and, if desired, f) alkylation of the deprotected compound with an alkylating reagent $R'_4Z$.

The asymmetric compounds of the isophthalic type (compounds of formula I in which $R_1 = -CO-N-R_7$
         |
         $R_8$ with $R_7 \neq R_2$ and/or $R_8 \neq R_3$) can be prepared by a) acylation of an amine of formula

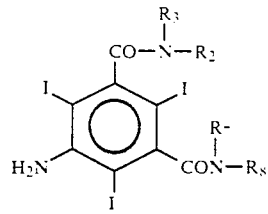 XVIII with an acid chloride of formula RCOCl, b) alkylation, if desired, with an alkylating reagent of formula $R'_4Z$ and c) removal of the protecting groups from the —CH—(CH$_2$OH)$_2$ group.

The compound of formula XVIII may be obtained as described in EP—0 015 867.

As an alternative, the asymmetric compounds of the isophthalic type can be prepared by a) acylation of an amine of formula:

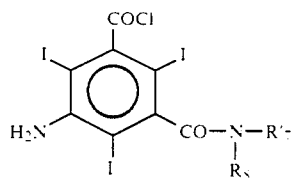 XIX in which $R'_7$ represents a $R_7$ group in which the hydroxy groups are protected, with an acid chloride of formula RCOCl (IV) so as to give rise to a compound of formula:

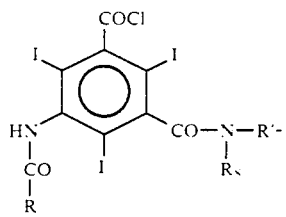 XX b) reaction of the compound of formula XX with an amine of formula:

 (VII)

so as to give to a compound of formula:

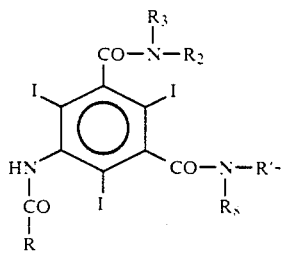 XXI then, if desired, either c) alkylation of the compound of formula XXI with an alkylating reagent of formula $R'_4Z$ such as that previously specified and finally d) removal of the protecting groups from the —CH—(CH$_2$OH)$_2$ group, or e) removal of the protecting groups from the —CH—(CH$_2$OH)$_2$ group, and, if desired, f) alkylation of the deprotected compound with an alkylating reagent R'$_4$Z.

Another subject of the present invention is contrast medium, which contain at least one compound of formula I.

These contrast media are used in man and animals for radiological purposes.

The preferred pharmaceutical form of the contrast materials according to the invention consists of aqueous solutions of the compounds.

The aqueous solutions usually contain a total of from 5 to 100 g of compounds of formula I per 100 ml and the volume of such solution to be injected usually varies from 1 to 1000 ml.

The aqueous solution of the compounds of formula I may also contain certain additives such as:

sodium chloride at concentrations included between 0.1 and 10 mM/l disodium EDTA at concentrations included between 0.1 and 2 mM/l sodium citrate at concentrations included between 0.1 and 10 mM/l heparin at doses included between 10 and 100 units per 100 ml of solution.

These compounds may be administered by all routes conventionally used for iodinated non-ionic contrast medium Thus, they may be administered by the enteral route or the parenteral route (intravenous route, intra-arterial route, opacification of the cavities) and in particular into the subarachnoid space.

An example of the composition according to the present invention will be given below.

| Composition | |
|---|---|
| Composition of example 1 | 65 g |
| Water for injectable preparation | |
| QS | 100 ml |

The following examples illustrate the preparation of the compounds of formula I.

Example 1

Preparation of
5-[3-hydroxy-2-(hydroxymethyl)-N-(2,3-dihydroxy-propyl)propionamido]-N',N'''-bis-(2-hydroxyethyl)-2,4,6-triiodo-isophthalamide a) Preparation of
5-[2-isopropyl-1,3-dioxane-5-carboxamido]-2,4,6-triiodo-isophthaloyl dichloride 137 g of 5-amino-2,4,6-triiodoisophthaloyl chloride (0.23 mole) are dissolved in 460 ml of DMAC to which are added 110 g (0.57 mole) of 2-isopropyl-1,3-dioxane-5-carboxylic acid chloride. The reaction mixture is stirred under argon at ambient temperature for 4 days. The DMAC is removed in a vacuum. The oil obtained is extracted with 3 l of ethyl acetate and washed twice with 1 l of ice-cold water. The organic phase is dried and concentrated to dryness. The product is crystallized from 200 ml of CH$_2$Cl$_2$. After filtration, 110 g of solid are obtained:

| | |
|---|---|
| Yield: 64% | |
| TLC: SiO$_2$ CH$_2$Cl$_2$ | Rf: 0.13 |
| (60 F 254) SiO$_2$ ether/petroleum ether 50/50 | |
| Rf: 0.52 | | b) Preparation of
5-[2-isopropyl-1,3-dioxane-5-carboxamido]-N',N'''-bis-(2-hydroxyethyl)-2,4,6-triiodo-isophthalamide 130 g of the product obtained in a (0.173 mole) are dissolved in a solution of 750 ml of DMAC and 75 ml (0.534 mole) of triethylamine. 33.7 g of ethanolamine (0.552 mole) are added dropwise to the reaction mixture. The reaction mixture is then stirred for 3 hours at ambient temperature. The triethylamine hydrochloride is removed by filtration and the DMAC is removed in a vacuum. The oil obtained is crystallized from 1 liter of water. The product is filtered off and dried in a vacuum.

| | | |
|---|---|---|
| Yield: 95% | | |
| TLC: SiO$_2$ Rf: 0.25 | | CH$_2$Cl$_2$/methanol 9 1 |
| (60F254) SiO$_2$ Rf: 0.67 | | CH$_2$Cl$_2$ methanol 8 2 |
| % I: 45.6 (found) - 47.6 (theory) | | |
| | | Hypersil C8 5μ 15 cm |
| HPLC purity: 97% | | 0.01M NaH$_2$PO$_4$ = 50 |
| | | Methanol = 50 | c) Preparation of
5-[3-hydroxy-2-hydroxymethyl-N-(2,3-dihydroxy-propyl)propionamido]-N',N'''-bis-(2-hydroxyethyl)-2,4,6-triiodo-isophthalamide To a suspension of 100 g of the product obtained in b (0.125 mole) in 350 ml of ethylene glycol are added dropwise 125 ml (0.5 mole) of 4N methylate at 60° C. followed by 65 g (0.625 mole) of 1-chloro-2,3-propanediol. After 1 hour at 60° C. the mass of the reaction mixture has increased. 100 ml (0.4 mole) of 4N methylate and 55.2 g (0.5 mole) of 1-chloro-2,3-propanediol are added. The mixture is maintained overnight at 60° C. A further addition of 31 ml (0.125 mole) of 4N methylate and 20.7 g of 1-chloro-2,3-propanediol is made. Stirring is maintained for 4 hours at 60° C. The mineral salts are removed by filtration. The ethylene glycol is evaporated in a vacuum.

The distillation residue is taken up in 800 ml of 10N HCl and the solution is stirred overnight at ambient temperature. The reaction mixture is concentrated to dryness and the residue is taken up in 300 ml of ethanol. The mineral salts are removed by filtration. The ethanol is evaporated in a vacuum and the residue is crystallized from 1 liter of isopropyl alcohol. The precipitate is filtered off and purified by HPLC (RP 18) (elution with water).

| | |
|---|---|
| Total yield (alkylation-deprotection-purification): 52% | |
| (1) TLC (silica 60F254): CH$_2$Cl$_2$/methanol 7 3 Rf: 0.4 | |
| (2) HPLC Hypersil C8 5μ 15 cm | |
| Buffer 0.01M NaH$_2$PO$_4$ | 97 |
| methanol | 3 |
| Purity: 97% | |
| (3) % I: 45.8 (found) - 46.4 (theory) | |
| (4) NMR (DMSO) | |

Poorly resolved multiplet centered at 3.5 ppm (18H); multiplet centered at 4.5 ppm (OH) exchangeable with D₂O (6 H); broad peak at 8.4 ppm (NH) exchangeable with D₂O (2 H).

EXAMPLE 2

Preparation of 5-qlycolamido-3-[3-hydroxy-2-hydroxymethyl-N-(2,3-dihydroxypropyl)propionamido]-2,4,6-triiodo-N-hydroxyethyl benzamide a) Preparation of 3,5-dinitro-N-(2-hydroxyethyl)benzamide 750 g (3.32 moles) of methyl 3,5-dinitro benzoate are suspended in 2 liters of methanol in the presence of 222.7 g (3.65 moles) of ethanolamine. The reaction mixture is refluxed for 48 hours until the ester has disappeared. After 4 hours at room temperature, the crystalline product is filtered off, washed with 500 cm³ of methylene chloride, then dried in an oven at 60° C. in a vacuum for 4 hours. This procedure leads to the recovery of 718 g of product in a yield of 85% Melting point: 140° C.

TLC (toluene/methyl ethyl ketone/formic acid (60/25/25) Rf: 0.5.

b) Preparation of 3-nitro 5-amino-N-(2-hydroxyethyl)benzamide

To a suspension of 25.5 g (0.5 mole) of 3,5-dinitro-N-(2-hydroxyethyl)benzamide in 135 cm³ of water are added at 70° C. 12.25 g (0.18 mole) of ammonium sulfide. At the end of the addition the mixture is homogenous but reprecipitation occurs after ½ hour at 70° C. The reaction mixture is allowed to cool to ambient temperature and stirring is continued for 2 hours. The precipitate is filtered off, washed with methanol (70 cm³) then dried in an oven (60° C.).

Mass obtained: 15.1 g —yield 67%.

TLC (toluene/methyl ethyl ketone/formic acid 60/25/25). Rf: 0.3

¹H NMR (DMSO): 3.4 ppm (multiplet; 4H,CH₂ aliphatics); 4.65 ppm (multiplet, H exchangeable with D₂O, NH₂); 5.9 ppm (singlet, H exchangeable with D₂O, OH); 7.4–7.7 ppm (2 multiplets; 3H, aromatic protons); 8.6 ppm (multiplet, 1H, NH).

c) Preparation of 3-nitro-5-[2-isopropyl-1,3-dioxane-5-carboxamido]-N-hydroxyethyl benzamide 40 g (0.177 mole) of 3-nitro-5-amino-N-(2-hydroxyethyl)benzamide are dissolved in 400 cm³ of DMAC. The addition of 74.9 g (0.389 mole) of 2-isopropyl-1,3-dioxane-5-carboxylic acid chloride in the presence of triethylamine (54.6 cm³) gives rise to an exothermic reaction.

The reaction mixture is maintained under argon for 18 hours at ambient temperature. The mixture is filtered and the filtrate is diluted with water and extracted with ethyl acetate. The residue obtained after evaporation of the solvent is treated with potassium carbonate (12 g) in 300 cm³ of methanol. After being stirred at ambient temperature for 48 hours, the mixture is concentrated, then extracted with ethyl acetate. The crude product obtained after treatment is recrystallized from a mixture of ether/ethyl acetate 80/20. 37.8 g of product are isolated in a yield of 56%.

TLC (ethyl acetate Rf: 0.48).
HPLC Hypersil C8 5μ 15 cm.
Buffer: 0.01M NaH₂PO₄ 50%
MeOH 50%
Purity: 94%.

d) Preparation of 5-amino-3-[2isopropyl-1,3-dioxane-5-carboxamido]-2,4,6-triiodo-N-hydroxyethyl-benzamide A methanolic solution (1.4 l) of 40 g of 3-nitro-5-[2-isopropyl-1,3-dioxane-5-carboxamido]-N-hydroxyethyl benzamide is stirred under an atmosphere of hydrogen (5.10⁵ Pa) for 5 hours at 50° C. in the presence of 4 g of palladized charcoal. The catalyst is then filtered off and the filtrate is evaporated under reduced pressure. The resulting compound is suspended in 950 cm³ of water. The mixture is made homogenous by the addition of 20 cm³ of 2N hydrochloric acid. 63 cm³ of iodine chloride (70% in iodine) are then added dropwise with vigorous stirring. After 24 hours at ambient temperature, the precipitate is filtered off, washed with water, taken up in ether. After drying, 32 g of product are obtained in a yield of 42%.

TLC (dichloromethane/methanol 90/10) Rf: 0.8.

e) Preparation of 5-amino-3-[N-(2,3-dihydroxypropyl)-2-isopropyl-1,3-dioxane-5-carboxamido]-2,4,6-triiodo-N-hydroxyethyl benzamide To a solution of the compound obtained in d) (20 g, 0.027 mole) in a mixture of ethylene glycol-dimethylformamide v/v (160 ml) are added dropwise 84 cm³ (0.337 mole) of 4N sodium methylate. The mixture is heated at 60° C. for ½ hour and 36.1 cm³ (0.432 mole) of 1-chloro-2,3-propanediol are added at this temperature. The reaction mixture is maintained at 60° C. under nitrogen for 60 hours. The mineral salts are removed by filtration. The ethylene glycol and the DMF are evaporated in a vacuum. The crude product obtained is purified on silanized silica (elution with water, followed by water/methanol 50/50). 16.5 g of product are isolated. Yield 76%.

TLC (dichloromethane/methanol 80/20). Rf: 0.8.

f) Preparation of 5-amino 3-[3-hydroxy-2(hydroxymethyl)-N-(2,3-dihydroxypropyl)propionamido]-2,4,6-triiodo-N-hydroxyethyl benzamide 16 g (0.02 mole) of the product obtained in e) are deprotected in the presence of 80 cm³ of 10N hydrochloric acid for 48 hours at ambient temperature. After neutralization and evaporation under reduced pressure, the residue is precipitated with a mixture of methanol-ether (9/1), filtered off then purified by HPLC (RP 18) (elution with water then with water/methanol 90/10).

4 g of product are isolated in an overall yield (deprotection, purification) of 30%.

TLC (dichloromethane/methanol 80/20). Rf: 0.25.
HPLC Hypersil C8 5μ 15 cm.
Buffer: 0.01M NaH₂PO₄ 90%
MeOH 10%
Purity: 97%.

g) Preparation of
5-N-qlycolamido-3-[3-hydroxy-2(hydroxymethyl)-N-(2,3-dihydroxypropyl)propionamido]-2,4,6-triiodo-N-hydroxyethyl benzamide 5.5 g of 0-acetylated glycolic acid chloride (0.04 mole) are added dropwise at ambient temperature to a solution of 3 g of the compound obtained in step f (0.004 mole) in 30 cm³ of anhydrous DMAC. The reaction mixture is heated at 40° C. for 12 hours, then poured into 250 cm³ of ice-cold water. The precipitate obtained is filtered off then extracted with ethyl acetate. After treatment followed by evaporation, the product obtained dissolved in 50 cm³ of methanol is deprotected in the presence of 10 cm³ of 1N sodium hydroxide. The solution is stirred at ambient temperature for 14 hours, then desalted by successive passages through H+ (IRN77) and OH⁻ (IRN78) resins. After evaporation to dryness, the residue is taken up in ethyl ether, filtered then dried.

Mass obtained: 1.5 g. Overall yield: 47%.
Purity in iodine: 99%.

TLC (ethyl acetate/methanol/ammonia 60/40/1).
Rf: 0.25.
HPLC Hypersil C8 5μ 15 cm.
Buffer: 0.01M NaH₂PO₄   90%
                MeOH    10%
Purity: 89%

EXAMPLE 3

Preparation of
3,5-bis-(3-hydroxy-2-hydroxymethyl-propionamido)-2,4,6-triiodo-N-(2,3-dihydroxypropyl)benzamide a) Preparation of
3,5-diamino-2,4,6-triiodo-N-(2,3-diacetoxypropyl)benzamide 301.5 g (0.5 mole) of 3,5-diamino-2,3,6-triiodo-N-(2,3-dihydroxypropyl)benzamide are suspended in 1 l of anhydrous pyridine cooled to 15° C. After the addition of 2450 ml of acetic anhydride, the solution is stirred for 18 h at ambient temperature, then poured into acidulated water. After extraction with ethyl acetate, drying of the organic phase and evaporation, 270 g of product are obtained in a yield of 78.5%.

Purity in iodine: 98.3%.
TLC toluene/methylethylketone/HCOOH 60/25/35. Rf: 0.70.

b) Preparation of
3,5-bis(2-isopropyl-1,3-dioxane-5-carboxamido)2,4,6-triiodo-N-(2,3-diacetoxypropyl)benzamide 114.5 g (0.166 mole) of the compound obtained in a) are dissolved in 350 ml of anhydrous DMAC. The addition of 128 g (0.66 mole) of 2-isopropyl-1,3-dioxane-5-carboxylic acid chloride is carried out at 0° C. After being stirred overnight the reaction mass is poured into a mixture of ice-water. The precipitate is filtered off, washed with water then dried in a vacuum at 50° C.

c) Preparation of
3,5-bis(2-isopropyl-1,3-dioxane-5-carboxamido)-2,4,6-triiodo-N(2,3-dihydroxypropyl) benzamide 175 g of the compound obtained in b) suspended in 2.5 l of methanol are stirred at ambient temperature in the presence of 45 g of potassium carbonate overnight. After evaporation of the reaction mixture, the product crystallizes from water. After filtration and drying, the crystals obtained in 85% yield are used directly in the next step.

d) Preparation of 3,5-bis(3-hydroxy-2-hydroxymethyl propionamido)-2,4,6-triiodo-N-(2,3-dihydroxypropyl)-benzamide The compound obtained in c) is dissolved in 2 l of 5N HCl at 50° C. After being stirred for 18 h, the suspension obtained is filtered. The filtrate is concentrated in a vacuum and the residue is taken up in isopropanol.

108 g of crystalline product are obtained in 2 crops in a yield of 94%.

TLC SiO₂ Butanol 60, water 25, CH₃COOH 11: Rf: 0.2.

The product is purified by preparative HPLC on SiO₂ RP18 15,25 u with water as eluant in a yield of 47%.

Purity in iodine: 99.6%.

HPLC purity: 99.1% (Hypersil C8 5μ 15 cm 0.01M NaH₂PO₄ 95, MeOH 5).

¹H NMR 200 MHz (DMSO): 8.5 ppm (m.1H exchangeable with D₂O, O-CONH); 9.9 ppm (t.2H exchangeable with D₂O, O-NH-CO); 4.6 ppm (m.6H exchangeable, OH); 3-4 ppm (m, 13H, CH); 2.7 ppm (m, 2H, NH—CH₂).

EXAMPLE 4

Preparation of
5-[3-hydroxy-2-(hydroxymethyl)-N-(2-hydroxyethyl)-propionamido]-N-(2-hydroxyethyl)-N'-(2,3-dihydroxypropyl)-2,4,6-triiodo-isophthalamide a) Preparation of
5-(2-isopropyl-1,3-dioxane-5-carboxamido)-2,4,6-triiodo-3-N'-(2-acetoxyethyl) carbamoyl-benzoyl chloride 5.36 g of 2-isopropyl-1,3-dioxane-5-carboxylic acid (0.0308 mole) are dissolved in 18 ml of DMAC. The reaction mixture is cooled to 5° C. and 2.55 ml (0.0350 mole) of SOCl₂ are added dropwise such that the temperature remains below 15° C. When the addition is complete, the reaction mixture is left for 3 hours at ambient temperature.

Then 6.0 g (0.00906 mole) of 5-amino-2,4,6-triiodo-3-(N-2-acetoxyethyl) carbamoyl-benzoyl chloride are added. The reaction mixture is maintained under argon for 4 days at ambient temperature.

The DMAC is removed in a vacuum. The oil obtained is taken up in ethyl acetate; the organic phase is washed with water, dried and concentrated to dryness. The product is crystallized from 100 ml of ether. After being filtered off and dried, 1.8 g of product are obtained in a yield of 24%.

TLC (silica 60F 254): ethyl acetate/petroleum ether 80/20-Rf=0.83.

b) Preparation of
5-(2-isopropyl-1,3-dioxane-5-carboxamido)-2,4,6-triiodo-N-(2-acetoxyethyl)-N'-(2,3-dihydroxypropyl)isophthalamide 1 g (0.00122 mole) of the product obtained in a is dissolved in 100 ml of DMAC, then 0.26 ml of triethylamine (0.00189 mole) are added. 0.18 g (0.00196 mole) of 3-amino-1,2-propanediol are added dropwise to the reaction mixture. After the addition is complete, the reaction mixture is stirred under argon at ambient temperature for 24 hours.

The triethylamine hydrochloride is filtered off, then the DMAC is evaporated. The oil thus obtained is crystallized from 20 ml of ether.

After being filtered off and dried, 0.8 g of product are obtained in a yield of 75.5%.

TLC (silica 60F254): CHCl$_3$/MeOH/NH$_4$OH 53/30/10 Rf=0.77.

c) Preparation of 5[3-hydroxy-2-(hydroxymethyl)-N-(2-hydroxyethyl)-propionamido]-N-(2-hydroxyethyl)-N'-(2,3-dihydroxypropyl)-2,4,6-triiodoisophthalamide 0.4 g (0.000458 mole) of the product obtained in b are dissolved in 0.7 ml of ethylene glycol and 0.69 ml (0.00275 mole) of a 4N solution of sodium methylate. To this solution is added 0.18 ml (0.00275 mole) of chloroethanol. The reaction mixture is heated at 40° C. for 5 hours. 0.34 ml of 4N sodium methylate and 0.1 ml of chloroethanol are added.

The mixture is maintained at 40° C. overnight.

The pH of the reaction mixture is brought to 7.00 by the addition of dilute hydrochloric acid.

The ethylene glycol is evaporated in a vacuum.

The residue after distillation is taken up in 6 ml of water and 5 ml of concentrated hydrochloric acid, then stirred overnight at ambient temperature.

The reaction mixture is concentrated then purified by preparative HPLC (RP 18, elution with water). After evaporation and drying, 0.1 g of product is obtained in an overall yield (alkylation-purification) of 27%.

TLC (silica 60F254): CH$_2$Cl$_2$/methanol/7/3-Rf=0.33.

HPLC: column of Hypersil C8 5μ 25 cm
Buffer: 0.01M NaH$_2$PO$_4$/MeOH: 95/5
Purity: 95%

$^1$H NMR (Bruker-200 MHz) in DMSO: in conformity with the expected structure.

EXAMPLE 5

Preparation of 5-[3-hydroxy-2-(hydroxymethyl)-propionamido]-N',N''-dimethyl]-bis-(2,3-dihydroxypropyl)-2,4,6-triiodoisophtalamide.

a) Preparation of [2-isopropyl-1,3-dioxanne-5-carboxamido]-N',N''-dimethyl-N',N'''-bis-(2,3-dihydroxypropyl)-2,4,6-triiodoisophtalamide.

74 g (98 mmoles) of 5-[2-isopropyl-1,3-dioxanne-5-carboxamido]-2,4,6-triiodoisophtaloyle dichloride are suspended in 300 ml of isopropanol containing 41 ml (294 mmoles) of triethylamine. 31 g (295 mmoles) of N-methyl-aminopropane-2,3-diol are added dropwise. Stirring is maintained 12 h at room temperature. Triethylamine hydrochloride is removed by filtration.

The filtrate is evaporated to dryness, taken up in water and eluted on resin OH$^-$ IRA 67.

After evaporation, the product is purified on silanized silica (Kieselgel 60 Merck) with water as eluent.

After evaporation to dryness, 60 g of white powder are obtained with a yield of 68.5%.

| | | |
|---|---|---|
| Purity in iodine = 96.4% | | |
| Purity HPLC: 97% | Hypersil CB 25 cm 5 um | |
| | NaH$_2$PO$_4$ 0.01M | 60 |
| | Methanol | 40 |
| TLC SiO$_2$. Rf | 0.12 | |
| | 0.25 | |
| | 0.30  0.36 | |
| Eluent CHCl$_3$ 55, MeOH 30, NH$_3$H$_2$O 10 | | |

RMN (DMSO) H 200 MHz: 0.9 ppm (d) CH$_3$ (6H); 2.8 ppm (s) N—CH$_3$ (3H); 3 ppm (s) N—CH$_3$ (3H); 3.3 ppm (m) N—CH$_2$ and CH (5H); 3.5–3.9 ppm (broad signal) CH$_2$ et. CH (8H); 4.3 ppm (q) CH (3H); 4.6 ppm (t) OH (2H); 4.7 ppm (d) OH (2H); 10.2 ppm (broadened signal) NH (1H).

b) Preparation of 5-[3-hydroxy-2-(hydroxymethyl)-propionamido]-N',N''-dimethyl-N',N''-bis-(2,3-dihydroxypropyl)-2,4,6-triiodoisophtalamide 45 g (50.6 mmole) of the compound disclosed in a) are dissolved in 101 ml (10 eq) of hydrochloric acid 5N. Stirring is maintained 12 h at room temperature. The solution is filtered and evaporated to dryness. The resulting product is taken up in 100 ml of ethyl ether and then filtered and eluted on silanized silica (Kieselgel 60 Merck) with water. After evaporation to dryness, 38 g of white powder are obtained.

| | | |
|---|---|---|
| Yield = 90% | | |
| Purity in iodine = 98.3% | | |
| Purity HPLC > | 98% Hypersil C8 25 cm 5 u | |
| | NaH$_2$PO$_4$ 0.01M | 95 |
| | MeOH | 5 |
| TLC SiO$_2$ Rf | 0.56 | |
| | 0.63 | |
| | 0.67 | |
| Eluent CHCl$_3$ 55, MeOH 30, NH$_3$, H$_2$O 10 | | |

RMN (DMSO) H 200 MHz: 2.7 ppm (broad signal) CH (1H); 2.85 ppm (broadened singlet) N—CH$_3$ (3H); 3.08 ppm (badly resolved doublet) N—CH$_3$ (3H); 3.10–3.35 ppm (m) N—CH$_2$; 3.45 ppm (q) CH$_2$ (4H); 3.6–4 ppm (broad signal) OH (6H); 9.9 ppm (broad signal) NH (1H).

EXAMPLE 6

Preparation of 5-[3-hydroxy-2(hydroxymethyl)-N-(2,3-dihydroxypropyl)-propionamido]-N',N'''-dimethyl]-N',N''-bis(2-hydroxyethyl)-2,4,6-triiodoisophtalamide a) Preparation of 5-[2-isopropyl-1,3-dioxanne-5-carboxamido]-N',N''-bis-(2-hydroxyethyl)-2,4,6-triiodo isophtalamide 0.126 mole of the product obtained in example 1a are suspended in 400 ml of isopropanol containing 53 ml of thriethylamine (0.378 m). 28.5 g (0.378 m) of N-methyl amino ethanol are added dropwise. Stirring is maintained 16 hours at room temperature.

Triethylamine hydrochloride is removed by filtration. The filtrate is evaporated to dryness and washed with 2×500 ml of water. The residue is taken up in 600 ml of isopropanol and filtered on activated carbon. The filtrate is concentrated to dryness and taken up in 600 ml of ethyl ether.

The precipitate is filtered and dried under vacuum.
Yield=82%
Purity HPLC=97%
TLC SiO$_2$
Eluent CH$_2$Cl$_2$ 9, methanol 1
Rf=0.37, 0.33, 0.27.

b) Preparation of 5-[3-hydroxy-2(hydroxymethyl)-N-(2,3-dihydroxypropyl)-propionamido]-N',N"-dimethyl-N',N"-bis(2-hydroxyethyl)-2,4,6-triiodoisophtalamide To a suspension of 20 g (0.0241 m) of the product obtained in 6a in 80 ml of Monoglyme are added dropwise 25.3 g (0.145 m) of 30.8% (W/W) sodium methylate at 35° C. Stirring is maintained 1 hour at this temperature.

16 g. of 1-chloro-2,3-propanediol (0.145 m) are added dropwise.

The mixture is maintained 24 hours at 35° C. Mineral salts are removed by filtration. Monoglyme is evaporated under vacuum. The distillation residue is taken up in 100 ml of HCl 5N and is maintained under stirring one night at room temperature. The reaction mixture is concentrated to dryness. The oily residue is purified by preparative HPLC (RP 18-elution by water and then water/methanol).

| HPLC > 95% | Hypersil CB 25cm 5μ | |
|---|---|---|
| | $NaH_2PO_4$ 0.01M | 90 |
| | Methanol | 10 |
| | 1 ml/m | |
| TLC $SiO_2$. Rf 0.16, 0.21, 0.28, 0.36 | | |
| Eluent water, acetic acid, butanol 25/11/5 | | |

RMN (DMSO) $^1H^{13}C$ 200 MHz in accordance with the expected structure.

We claim:

1. A compound of the formula:

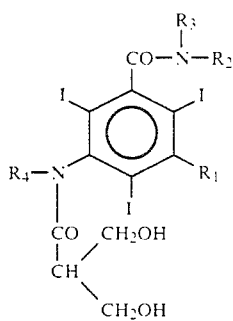

in which $R_1$ is selected from a group of the formula

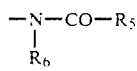

in which
$R_5$ is selected from $C_1$-$C_4$ alkyl, $C_1$-$C_4$ hydroxyalkyl and $C_1$-$C_4$ polyhydroxyalkyl, and
$R_6$ is selected from hydrogen, $C_1$-$C_4$ alkyl, $C_1$-$C_4$ hydroxy alkyl and $C_1$-$C_4$ polyhydroxyalkyl,
and a group of the formula

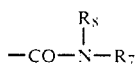

in which
$R_7$ is selected from $C_1$-$C_4$ hydroxyalkyl and $C_1$-$C_4$ polyhydroxyalkyl, and
$R_8$ is selected from hydrogen and $C_1$-$C_4$ alkyl, $R_2$ is selected from $C_1$-$C_4$ hydroxyalkyl and $C_1$-$C_4$ polyhydroxyalkyl,
$R_3$ is selected from hydrogen and $C_1$-$C_4$ alkyl, and
$R_4$ is selected from hydrogen, $C_1$-$C_4$ alkyl, $C_1$-$C_4$ hydroxyalkyl and $C_1$-$C_4$ polyhydroxyalkyl.

2. A compound according to claim 1, having the formula:

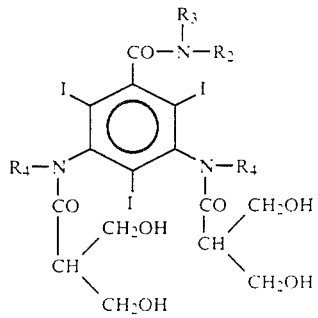

in which $R_2$, $R_3$ and $R_4$ have the meanings given in claim 1.

3. A compound according to claim 1 which is 5-[3-hydroxy-2-(hydroxymethyl)-N-(2,3-dihydroxypropyl)-propionamido]-N',N"-bis-(2-hydroxyethyl)-2,4,6-triiodoisophthalamide.

4. A compound according to claim 1 which is 5-glycolamido-3-[3-hydroxy-2-(hydroxymethyl)-N-(2,3-dihydroxypropyl)propionamido]-2,4,6-triiodo-N-hydroxyethyl benzamide.

5. A compound according to claim 1 which is 3,5-bis-(3-hydroxy-2-hydroxymethyl-propionamido-2,4,6-triiodo-N-(2,3-dihydroxypropyl) benzamide.

6. A compound according to claim 1 which is 5-[3-hydroxy-2-(hydroxymethyl)-N-(2-hydroxyethyl)-propionamido]-N-(2-hydroxyethyl)-N'-(2,3-dihydroxypropyl)-2,4,6-triiodo-isophthalamide.

7. A compound according to claim 1 which is 5-[3-hydroxy-2-(hydroxymethyl)-propionamido]-N', N"-dimethyl]-N',N"-bis-(2,3-dihydroxypropyl)-2,4,6-triiodoisophtalamide.

8. A compound according to claim 1 which is 5-[3-hydroxy-2(hydroxymethyl)-N-(2,3-dihydroxypropyl)-propionamido]-N',N"-dimethyl-N',N"-bis(2-hydroxyethyl)-2,4,6-triiodoisophtalamide.

9. A contrast medium comprising an effective amount of at least one compound according to claim 1, in admixture with a pharmacologically acceptable excipient, said amount being effective to provide contrast during radiography.

10. A contrast medium according to claim 9, comprising an aqueous solution of the compound(s).

11. A compound of the formula:

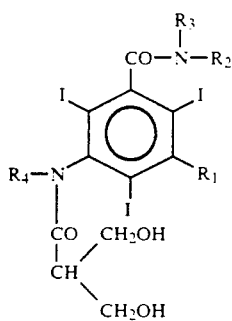

in which $R_1$ is selected from a group of the formula

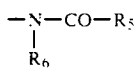

in which $R_5$ is selected from $C_1$-$C_4$ alkyl, $C_1$-$C_4$ hydroxyalkyl and $C_1$-$C_4$ polyhydroxyalkyl, and $R_6$ is selected from hydrogen, $C_1$-$C_4$ alkyl, $C_1$-$C_4$ hydroxyalkyl and $C_1$-$C_4$ polyhydroxyalkyl;

and a group of the formula

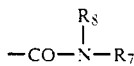

in which $R_7$ is selected from $C_1$-$C_4$ hydroxyalkyl and $C_1$-$C_4$ polyhydroxyalkyl, and $R_8$ is selected from hydrogen and $C_1$-$C_4$ alkyl, $R_2$ is selected from hydrogen, $C_1$-$C_4$ hydroxyalkyl and $C_1$-$C_4$ polyhydroxyalkyl, $R_3$ is selected from hydrogen and $C_1$-$C_4$ alkyl, and $R_4$ is selected from hydrogen, $C_1$-$C_4$ alkyl, $C_1$-$C_4$ hydroxyalkyl and $C_1$-$C_4$ polyhydroxyalkyl.

12. A contrast media comprising an effective amount of at least one compound according to claim 11, in admixture with a pharmacologically acceptable excipient, said amount being effective to provide contrast during radiography.

* * * * *